United States Patent
Herrmann et al.

(10) Patent No.: US 6,888,002 B2
(45) Date of Patent: May 3, 2005

(54) TRANSITION METAL COMPLEXES WITH DIAMINOCARBENE LIGANDS AND THEIR USE IN REACTIONS CATALYZED BY TRANSITION METALS

(75) Inventors: Wolfgang A. Herrmann, Freising (DE); Karin Denk, München (DE)

(73) Assignee: Bayer Aktiengesellschaft, Leverkusen (DE)

( * ) Notice: Subject to any disclaimer, the term of this patent is extended or adjusted under 35 U.S.C. 154(b) by 138 days.

(21) Appl. No.: 10/261,326

(22) Filed: Sep. 30, 2002

(65) Prior Publication Data

US 2003/0119660 A1 Jun. 26, 2003

(30) Foreign Application Priority Data

Oct. 2, 2001 (DE) .......................... 101 48 722

(51) Int. Cl.⁷ .......................... C07F 15/00; B01J 31/00
(52) U.S. Cl. .......................... 548/103; 556/22; 556/46; 556/58; 556/59; 556/60; 556/136; 556/137; 556/140; 556/141; 556/478; 548/109

(58) Field of Search .............................. 556/22, 46, 58, 556/59, 60, 136, 137, 140, 141, 478; 548/103, 109

(56) References Cited

U.S. PATENT DOCUMENTS

| 5,728,839 A | 3/1998 | Herrmann et al. .......... 548/103 |
| 6,316,380 B1 | 11/2001 | Nolan et al. ................. 502/155 |
| 6,403,802 B1 | 6/2002 | Nolan et al. ................. 548/103 |

FOREIGN PATENT DOCUMENTS

WO 00/71554 11/2000

OTHER PUBLICATIONS

Romerosa et al.: Inorg. Chem., Bd. 36, 1997, Seiten 3784–3786, XP002225825 Seite 3785 Abbildung 2.

Primary Examiner—Porfirio Nazario-Gonzalez
(74) Attorney, Agent, or Firm—Godfried R. Akorli; Jill Denesvich

(57) ABSTRACT

The invention relates to novel transition metal complexes containing at least one diaminocarbene ligand, to processes for preparing these transition metal complexes and to their use as catalysts in organic reactions.

13 Claims, No Drawings

TRANSITION METAL COMPLEXES WITH DIAMINOCARBENE LIGANDS AND THEIR USE IN REACTIONS CATALYZED BY TRANSITION METALS

BACKGROUND OF THE INVENTION

1. Field of the Invention

The invention relates to novel transition metal complexes containing at least one diaminocarbene ligand, to processes for preparing these transition metal complexes and to their use as catalysts in organic reactions.

2. Brief Description of the Prior Art

Transition metal-carbene complexes have been known for a long time and are important reagents in the field of synthetic organic chemistry. Transition metal-carbene complexes are used, inter alia, as catalysts in organic reactions.

In Synth. Meth. Organomet. Inorg. Chem. 9, 2000, 84–112, Herrmann et al. describe N-heterocyclic transition metal-carbene complexes and use, for example, palladium (0)-carbene complexes as catalysts for Heck reactions and state that Ru(II)-carbene complexes are promising catalysts for reactions involving C—C or C—H bond formation.

WO 00/15339 A1 describes carbene complexes of ruthenium and of osmium which can be used as catalysts in olefin metathesis.

Despite the fact that transition metal-carbene complexes suitable as catalysts in organic synthetic reactions are known, there is a need for new transition metal-carbene complexes which can be used, in particular, as catalysts in organic synthetic reactions and have not only high activities but also long catalyst operating lives so that they can be used in large-scale industrial syntheses.

SUMMARY OF THE INVENTION

We have now surprisingly found compounds of the general structural formula (I),

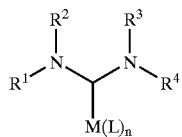

(I)

where
M is a transition metal of transition groups 6 to 8 of the Periodic Table,
the radicals $R^1$, $R^2$, $R^3$ and $R^4$ are identical or different and are hydrogen and/or hydrocarbon groups, where the hydrocarbon groups may be identical or different, straight-chain, branched or cyclic radicals selected from the group consisting of alkyl radicals having from 1 to 50 carbon atoms, alkenyl radicals having from 2 to 50 carbon atoms, alkynyl radicals having from 2 to 50 carbon atoms and aryl radicals having from 6 to 30 carbon atoms in which at least one hydrogen atom may be replaced by a functional group, and/or
$R^1$ and $R^2$ and/or $R^3$ and $R^4$ are part of a cyclic system which is identical or different, where the cyclic system comprises a carbon framework having from 2 to 20 carbon atoms and a nitrogen atom in formula (I), where the carbon atoms of $R^1$ and $R^2$ and/or $R^3$ and $R^4$ in formula (I) are not counted and where at least one hydrogen atom in the ring may be replaced by a functional group and/or at least one carbon atom of the ring may be replaced by a heteroatom selected from the group consisting of S, P, O and N, and/or
$R^1$ and/or $R^2$ and/or $R^3$ and/or $R^4$ are linked to one of the ligands L via a bridge having from 1 to 20 carbon atoms, where the carbon atoms of $R^1$, $R^2$ $R^3$ and $R^4$ are not counted, and
L are identical or independently different uncharged two-electron donors and/or are parts of a cyclic system and/or are anionic ligands, and
n is an integer, preferably from 0 to 6, particularly preferably from 2 to 4.

DETAILED DESCRIPTION OF THE INVENTION

The compounds of the invention have at least one diaminocarbene ligand of the type $R^1R^2N$—C—$NR^3R^4$ as a structural feature and possess surprisingly long catalyst operating lives. This advantage is particularly evident in reactions which proceed in the temperature range above 100° C. The compounds of the invention also have extraordinary thermal stabilities and a high catalyst activity.

If L in the novel compounds of the general formula (I) represents identical or independently different uncharged two-electron donors, the ligands in question are preferably ligands selected from the group consisting of amines, imines, phosphines, phosphites, stibines, arsines, CO, carbonyl compounds, nitrites, alcohols, thiols, ethers, thioethers and pyridines.

Furthermore, L preferably represents identical or independently different uncharged two-electron donor ligands selected from the group consisting of N-heterocyclic carbenes of the general formulae (A–E)

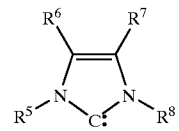

A

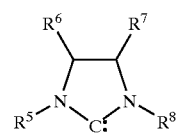

B

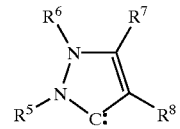

C

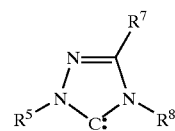

D

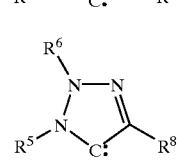

E where
the radicals $R^5$, $R^6$, $R^7$ and $R^8$ are identical or different and are hydrogen and/or hydrocarbon groups, where the hydrocarbon groups are identical or different, straight-chain, branched or cyclic radicals selected from the group consisting of alkyl radicals having from 1 to 50 carbon atoms, alkenyl radicals having from 2 to 50 carbon atoms, alkynyl radicals having from 2 to 50 carbon atoms and aryl radicals having from 6 to 30 carbon atoms in which at least one hydrogen atom may be replaced by a functional group, and/or the radicals $R^6$ and $R^7$ are identical or independently different halogen, nitro, nitroso, alkoxy, aryloxy, amido, carboxyl, carbonyl, thio or/and sulfonyl groups.

Furthermore, L preferably represents identical or independently different uncharged two-electron donor ligands selected from the group consisting of diaminocarbene ligands of the general formula (II),

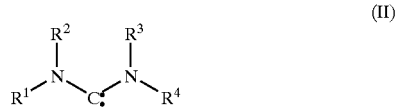

(II)

where
the radicals $R^1$, $R^2$, $R^3$ and $R^4$ are as defined above.

Furthermore, L preferably represents identical or independently different uncharged two-electron donor ligands selected from the group consisting of compounds of the general formulae (III) and (IV)

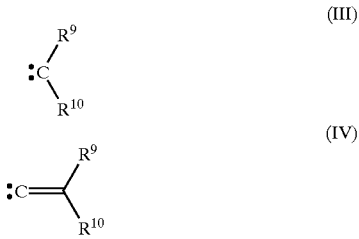

(III)

(IV)

where
the radicals $R^9$ and $R^{10}$ are identical or different and are hydrogen or/and hydrocarbon groups, where the hydrocarbon groups are identical or different, straight-chain, branched or cyclic radicals selected from the group consisting of alkyl radicals having from 1 to 50 carbon atoms, alkenyl radicals having from 2 to 50 carbon atoms, alkynyl radicals having from 2 to 50 carbon atoms, aryl radicals having from 6 to 30 carbon atoms and silyl radicals in which at least one hydrogen atom may be replaced by an alkyl, aryl, alkenyl, alkynyl, metallocenyl, halogen, nitro, nitroso, hydroxy, alkoxy, aryloxy, amino, amido, carboxyl, carbonyl, thio or/and sulfonyl group.

If L in the novel compounds of the general formula (I) is part of a cyclic system, the cyclic system is preferably a cyclic diene, preferably a diene having from 5 to 10 carbon atoms, very particularly preferably 1,5-cyclooctadiene.

If L in the novel compounds of the general formula (I) represents identical or independently different anionic ligands, the ligands concerned are preferably ligands selected from the group consisting of halides, pseudohalides, hydroxides, alkoxides, thiolates, carboxylates and sulfonates, with preferred pseudohalides being cyanide, thiocyanate, cyanate, isocyanate and isothiocyanate.

In a preferred embodiment of the novel compounds of the general formula (I), M is rhodium or iridium and n is 3, with $L^1$, $L^2$ and $L^3$ being identical or independently different and/or being part of a cyclic system, where $L^1$ is an anionic ligand selected from the group consisting of halide, alkoxide, carboxyl compound, thiolate and pseudohalide or is an uncharged two-electron donor selected from the group consisting of alkenes, alkynes, phosphines, amines, imines, phosphites, stibines, arsines, CO, carbonyl compounds, nitriles, alcohols, ethers, thiols and thioethers and $L^2$ and $L^3$ are identical or independently different and are uncharged two-electron donor ligands selected from the group consisting of alkenes, alkynes, phosphines, amines, imines, phosphites, stibines, arsines, CO, carbonyl compounds, nitriles, alcohols, ethers, thiols and thioethers or, in a preferred embodiment, are part of a cyclic diene; particular preference is given to $L^2$ and $L^3$ together representing 1,5-cyclooctadiene.

In a particularly preferred embodiment of the novel compounds of the general formula (I) M is rhodium or iridium and n is 3 and $L^2$ and $L^3$ together represent a cyclic diene, very particularly preferably 1,5-cyclooctadiene, and $L^1$ is halide or CO, with the charge on monovalent or trivalent rhodium or iridium being balanced and the resulting coordination numbers being 4, 5 or 6.

In a further preferred embodiment of the novel compounds of the general formula (I), M is ruthenium or osmium and n is 4 and $L^1$ and $L^2$ are identical or independently different and are each an anionic ligand selected from the group consisting of halide, alkoxide, carboxyl compound, thiolate and pseudohalide, with preferred pseudohalides being cyanide, thiocyanate, cyanate, isocyanate and isothiocyanate, $L^3$ is a carbene ligand of the general formula (III) or (IV) and $L^4$ is an uncharged two-electron donor ligand selected from the group consisting of amines, imines, phosphines, phosphites, stibines, arsines, CO, carbonyl compounds, nitriles, alcohols, thiols, ethers and thioethers or is an uncharged two-electron donor selected from the group consisting of N-heterocyclic carbenes of the general formulae A–E or a diaminocarbene ligand of the general formula (II).

If $L^4$ is a diaminocarbene ligand of the general formula (II), then $R^1$ and $R^2$ and/or $R^3$ and $R^4$ are preferably part of a cyclic system comprising a carbon framework having from 2 to 20 carbon atoms, preferably 2 to 10 carbon atoms, and a nitrogen atom in formula (II), with the carbon atoms of $R^1$ and $R^2$ and/or $R^3$ and $R^4$ in formula (II) not being counted and at least one hydrogen atom in the ring being able, if desired, to be replaced by a functional group. In the event of more than one such cyclic system, these may be identical or different.

In a further, particularly preferred embodiment of the novel compounds of the general formula (I), M is ruthenium or osmium and n is 4 and $L^1$ and $L^2$ are identical or different and are each chloride, bromide or iodide, $L^3$ is a carbene ligand of the general formulae (III) or (IV) and $L^4$ is a phosphine, preferably trimethylphosphine, tricyclohexylphosphine or triphenylphosphine, and are chosen so that the charge on the divalent, tetravalent or hexavalent ruthenium or osmium is balanced and the resulting coordination number is 4, 5 or 6.

In a further, preferred embodiment of the novel compounds of the general formula (I), M is Cr and n is 4 and the ligands $L^1$ to $L^4$ are identical or different and are uncharged two-electron donor ligands such as CO, phosphine, phosphite, stibine, arsine, alkene, alkyne, amine, imine, carbonyl compounds, nitrile, alcohol, ether, thiol, thioether or nitrile; it is very particularly preferred that $L^1$ to $L^4$ are identical and are each CO.

Various methods known from the literature for the preparation of transition metal complexes with saturated or unsaturated N-heterocyclic carbene ligands are in principle available for the synthesis of the compounds of the invention. Such methods include reaction of suitable transition metal precursors with the free ligands of the type $R^1R^2N—C—NR^3R^4$ which can be prepared from the corresponding formamidinium salts $[R^1R^2N—CH=NR^3R^4]^+X^-$ or with the formamidinium salts themselves (salt metathesis). These methods were applied successfully to diaminocarbene ligands for the first time in the present invention. The novel compounds of the formula (I) concerned were not expected to be stable systems according to the prior art.

To prepare novel compounds of the formula (I) in a ligand exchange reaction via free carbene, preference is given to reacting the free carbene ligand of the general formula (II) with suitable transition metal complexes, with the free carbene being prepared from the formamidinium salt by deprotonation with strong bases such as lithium diisopropylamide (Angew. Chem. 1996, 108, 1211; Angew. Chem Int. Ed. Engl. 1996, 35, 1121; Tetrahedron 1999,55 14523–14534), but particularly preferably by the "ammonia method" described in DE 196 10 908 A1.

To prepare the novel compounds of the formula (I) by salt metathesis, the formamidinium salts are reacted with suitable transition metal complexes.

However, it is also possible to generate the carbene of the general formula (II) in situ as an intermedium from the alkoxide adduct of the formamidinium salt with alkali metal alkoxides, preferably potassium tert-butoxide, by brief heating. This intermediate then undergoes a ligand exchange reaction with appropriate transition metal complexes to form the compounds of the invention (WO 00/71554 A2 and WO 00/15339 A1).

The preparation of the novel compounds of the formula (I) is preferably carried out by the following methods:

a) Ligand Exchange Reaction via Free Carbene:

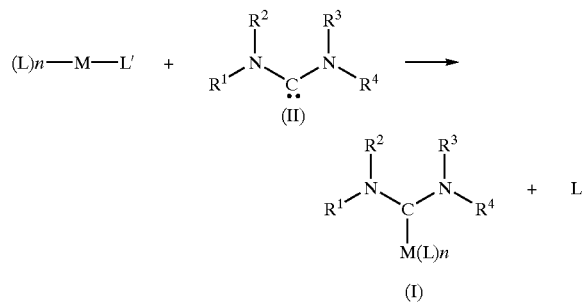

L' is preferably an uncharged exchange ligand such as nitrile or phosphine. The ligand exchange reaction is preferably used for the preparation of the novel compounds of the formula (I) in which M is ruthenium or osmium.

b) Salt Metathesis:

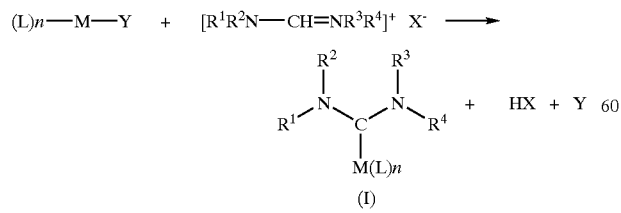

Y is preferably an uncharged or anionic exchange ligand, for example, amine, halide, acetate, acetylacetonate or alkoxide. Salt metathesis is preferably used for the preparation of the novel compounds of the formula (I) in which M is rhodium or iridium.

c) Alkoxide Adduct Method (Generation of the Carbene in situ):

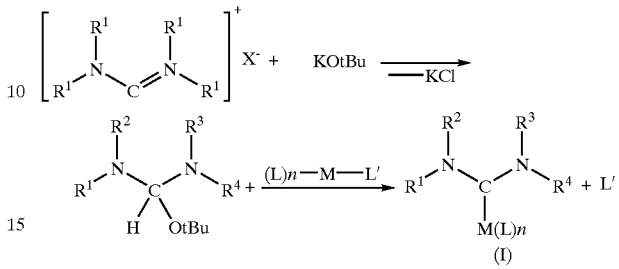

L' is preferably an uncharged exchange ligand such as nitrile or phosphine. The ligand exchange reaction is preferably used for the preparation of the novel compounds of the formula (I) in which M is ruthenium or osmium.

The compounds of the invention are preferably used as catalysts in organic synthetic reactions, for example, as catalysts for hydrosilylation, hydroformylation, olefin metathesis, alkyne metathesis, Heck coupling, Suzuki coupling, Sonogashira coupling, cyclopropanation or Grignard cross-coupling. Preference is given to using novel compounds of the formula (I) in which M is ruthenium or osmium in olefin metathesis. Further preference is given to using novel compounds of the formula (I) in which M is rhodium or iridium in hydrosilylation. The compounds of the invention can be used both as homogeneous catalysts and as heterogeneous catalysts. The latter embodiment is preferably achieved by the compounds of the invention being bound to a solid phase, for example, a polymeric support. The compounds of the invention are preferably bound to the solid phase via one or more ligands L, preferably via a ligand L selected from the group consisting of N-heterocyclic carbenes of the general formulae A–E and/or via a diaminocarbene ligand of the general formula (II).

The compounds of the invention are highly active and particularly inexpensive catalysts which can be synthesized in good yield. Furthermore, the catalytic activity and selectivity of the compounds of the present invention can be controlled via the wide variety of possible ligand spheres, especially by variation of the diaminocarbene ligand $R^1R^2N—C—NR^3R^4$.

The advantage of these novel complexes compared with phosphine-containing or/and mixed phosphine-/N-heterocyclic carbene-containing complexes is the inexpensive preparation of the diaminocarbene ligands. The stability, selectivity and activity of the catalysts can be increased significantly compared with existing systems.

EXAMPLES

The following examples illustrate the invention, but do not restrict its scope.

Example 1

Precursors for Preparing the Complexes of the Invention

Tetramethylformamidinium chloride is commercially available. Tetraisopropylformamidinium chloride was synthesized by the method described in Angew. Chem. 1996, 108, 1211 and Angew. Chem. Int. Ed. Engl., 1996, 35, 1121.

a) Preparation of Dipiperidylformamidinium Chloride:

6.08 g (0.05 mol) of piperidinium chloride, 4.26 g (0.05 mol) of piperidine and 7.41 g (0.05 mol) of triethyl orthoformate were refluxed in 25 ml of ethanol for 4 hours. After cooling overnight, the volatile constituents were removed in a high vacuum. The residue was washed with 20 ml of THF (tetrahydrofuran) and subsequently extracted with 100 ml of a mixture of 20% by volume of ethanol and 80% by volume of ethyl acetate. The extract was dried over magnesium sulfate. Removal of the solvent in a high vacuum gave dipiperidylformamidinium chloride as a slightly yellowish, very hygroscopic solid.

$^1$H NMR (CDCl$_3$, 25° C.): δ=7.94 (1H, s, NCHN), 3.03, 3.36 (8H, m, NCH$_2$), 1.5–0.91 (m, 12H, residual CH$_2$).

$^{13}$C NMR (CDCl$_3$, 25° C.): δ=154.3 (NCHN), 51.9, 44.4 (NCH$_2$), 25.5, 22.7, 22.2 (NCH$_2$CH$_2$CH$_2$CH$_2$CH$_2$).

b) Preparation of Dipiperidylformamidinium Tetrafluoroborate 5 ml (0.01 mol) of piperidine, 2.6 g (0.025 mol) of ammonium tetrafluoroborate and 40 ml of triethyl orthoformate were refluxed for 2 hours. Ethanol formed was distilled off. Two phases were formed during this time. After cooling, the lower yellow phase was taken up in methylene chloride and dried over magnesium sulfate. Removal of the solvent in a high vacuum gave dipiperidylformamidinium tetrafluoroborate as a slightly yellowish, very hygroscopic solid.

Example 2

Synthesis of the Free Carbenes a) Deprotonation with NaH/NH$_3$(l) (Ammonia Method)

10 mmol of the corresponding formamidinium chloride or tetrafluoroborate together with about 20 ml of THF were placed in a reaction vessel. After about 20 ml of ammonia had been condensed onto this, 11 mmol of NaH were added. A slightly yellowish solution was formed over the course of about 2 hours. Firstly the ammonia and then the THF were subsequently removed in a high vacuum and the free carbene was extracted with hexane. The solution obtained in this way can be directly used further.

b) Deprotonation of the Formamidinium Salts With Lithium Diisopropylamide

A solution of 10 mmol of the corresponding formamidinium chloride or tetrafluoroborate in 15 ml of THF was slowly added dropwise at −78° C. to a solution of 10 mmol of lithium diisopropylamide in 15 ml of THF. The solution was slowly warmed to room temperature over a period of two hours. This resulted in formation of a clear, slightly yellowish solution. The solvent was removed in a high vacuum. The residue was extracted three times with 15 ml each time of toluene. The solution obtained in this way is directly used further.

Example 3

Synthesis of the Complexes of the Invention a) Synthesis of the Rh/Ir Compounds by Means of a Ligand Exchange Reaction I) Chloro(η$^4$-1,5-cyclooctadiene)(bis(diisopropylamino)carbene)rhodium(I)

A solution of bis(diisopropylamino)carbene (340 mg, 1.71 mmol, 2 eq) in THF (20 ml) was added dropwise to a solution of bis[μ-chloro(1,5-cyclooctadiene)rhodium] (421 mg, 0.85 mmol, 1 eq) in 40 ml of THF. The colour changed from light yellow to dark yellow. After stirring at room temperature for 30 minutes, the solvent was removed under reduced pressure. The precipitate was washed with ice-cold diethyl ether (2×10 ml) and dried under reduced pressure.

Yield: 533 mg, 71%. $^1$H NMR (400 MHz, CDCl$_3$, 20° C.): δ=5.16 (2H, cod$_{vinyl}$), 4.73 (1H, cod$_{vinyl}$), 4.09 (4H, NCH), 3.09 (1H, cod$_{vinyl}$), 2.35 (4H, cod$_{allyl}$), 1.74–1.17 (m, 28H, cod$_{allyl}$, CH$_3$).

$^{13}$C{$^1$H} NMR (100.1 MHz, CDCl$_3$, 20° C.): δ=233.6 (NCN, d, $^1$J(C—Rh)=67.8 Hz), 97.5, 67.3, 32.5, 30.9, 28.6 (cod), 56.4 (NCH), 23.8 (CH$_3$).

MS (Cl) m/e=458 (M$^+$, correct isotope pattern), 423 (M-Cl, correct isotope pattern), 314 (M-Cl-cod, correct isotope pattern).

Elemental analysis: (C$_{21}$H$_{40}$ClN$_2$Rh, 458.92): calculated: C, 54.96, H, 8.78, N, 6.10; found: C, 54.90, H, 8.81, N, 6.17.

II) Chloro(θ$^4$-1,5-cyclooctadiene)(bisdiisopropylaminocarbene)iridium(I)

Using a method analogous to that for the synthesis of the rhodium complex, bis[μ-chloro(1,5-cyclooctadiene)iridium (I)] (340 mg, 1.00 mmol, 1 eq) was reacted with bis (diisopropylamino)carbene (200 mg, 1.00 mmol, 2 eq) to form the desired complex. Yield: 746 mg, 68%.

$^1$H NMR (400 MHz, CDCl$_3$, 20° C.): δ=5.13 (2H, cod$_{vinyl}$), 4.73 (2H, cod$_{vinyl}$), 3.85 (4H, NCH), 2.95 (4H, cod$_{allyl}$), 2.11 (m, 4H, cod$_{allyl}$), 1.58–1.17 (m, 24H, CH$_3$).

$^{13}$C{$^1$H} NMR (100.1 MHz, CDCl$_3$, 20° C.): δ=225.6 (NCN), 82.1, 67.9, 33.2, 31.9, 29.2 (cod), 51.1 (NCH), 23.8 (CH$_3$).

MS (Cl) m/e=548 (M$^+$, correct isotope pattern).

Elemental analysis: (C$_{21}$H$_{40}$ClN$_2$Ir, 548.23), calculated: C, 46.01, H, 7.35, N, 5.11; found: C, 46.09, H, 7.41, N, 5.07.

b) Synthesis of the Rh/Ir Complexes by Salt Metathesis

I) Chloro(η$^4$-1,5-cyclooctadiene)(bis(diisopropylamino)-carbene)rhodium(I)

A 1 M solution of sodium methoxide (2.48 ml) was added dropwise to a suspension of bis[μ-chloro(1,5-cyclooctadiene)rhodium(I)] (300 mg, 0.61 mmol, 1 eq) in ethanol (30 ml). Over a period of 5 minutes, the color changed to lemon yellow owing to the formation of bis[μ-ethoxy(1,5-cyclooctadiene)rhodium(I)]. After stirring at room temperature for a further 10 minutes, bis(diisopropyl) formamidinium chloride (400 mg, 1.22 mmol, 2 eq) was added. The color changed to dark yellow. After stirring at room temperature for a further 30 minutes, the volatile constituents were removed under reduced pressure and the crude product was washed with ice-cold diethyl ether (2×10 ml) and dried. Yield: 531 mg, 68%.

II) Chloro(η$^4$-1,5-cyclooctadiene) (bisdiisopropylaminocarbene)iridium(I)

Using a method analogous to Example 3b, 1), bis[μ-chloro(1,5-cyclooctadiene)iridium(I)] (333 mg, 0.61 mmol, 1 eq), 1M sodium methoxide solution (2.48 ml) and bis (diisopropyl)formamidinium chloride (400 mg, 2 eq) were reacted to form the desired iridium compound in a yield of 71%.

c) Synthesis of the Rh/Ir Complexes via an Alkoxide Adduct

I) Chloro(η$^4$-1,5-cyclooctadiene)(bis(diisopropyl amino)-carbene)rhodium(I)

A solution of potassium tert-butoxide (191 mg, 1.70 mmol, 2.8 eq) in THF (20 ml) was added dropwise to a suspension of bis(diisopropyl)formamidinium chloride (280 mg, 1.70 mmol, 2.8 eq) in THF (30 ml) at room temperature, resulting in the formamidinium chloride dissolving slowly and the color changing to light yellow. After stirring at room temperature for 30 minutes, bis[μ-chloro(1,5-cyclooctadiene)rhodium(I)] (300 mg, 0.61 mmol, 1 eq) and toluene (30 ml) were added. The reaction solution was stirred at 80° C. for 1 hour. The volatile constituents were then removed under reduced pressure and the desired product was extracted with 60 ml of hexane. Drying gave the complex in a yield of 73%.

II) Chloro($\eta^4$-1,5-cyclooctadiene)(bis(diisopropylamino)-carbene)iridium(I)

Using a method analogous to Example 3c, I), bis[$\mu$-chloro(1,5-cyclooctadiene)-iridium(I)] (333 mg, 0.61 mmol, 1 eq), KOtBu (191 mg, 1.70 mmol, 2.8 eq) and bis(diisopropyl)formamidinium chloride (280 mg, 1.70 mmol, 2.8 eq) were reacted to form the desired iridium compound in a yield of 66%.

d) Synthesis of a Cr Complex by Means of a Ligand Exchange Reaction

I) Tetracarbonyl(bisdiisopropylaminocarbene)chromium(0)

A solution of 390 mg (1.6 mmol) of $Cr(CO)_6$ in 50 ml of THF was irradiated by a mercury vapor lamp (150 W) at room temperature for 3.5 hours while stirring. 200 mg (0.94 mmol) of bis(diisopropylamino)carbene were dissolved in 5 ml of tetrahydrofuran and added dropwise to the orange solution while stirring vigorously. After stirring at room temperature for a further 30 minutes, the color of the reaction solution changed to reddish brown. The solvent was distilled off under reduced pressure and excess $Cr(CO)_6$ was removed by sublimation in high vacuum. The brown residue was extracted three times with 20 ml each time of diethyl ether, the combined extracts were evaporated to 5 ml and then chromatographed on a 50 cm×1.0 cm silica gel column made up using hexane. After a pale yellow zone had been eluted with hexane/diethyl ether (2:1) (contains mainly $Cr(CO)_6$), the product could be eluted as a dark yellow band by means of diethyl ether. The product fractions were evaporated to 1–2 ml under reduced pressure and, after addition of 5–10 ml of hexane, the chromium complex precipitated at 0° C. in the form of dark yellow crystals which could be recrystallized from diethyl ether/hexane. Yield: 80 mg (23%)

$^1$H-NMR (400.13 MHz, $C_6D_6$): $\delta$ 0.942 (br. $CH_3$, 24H), 2.961 (br, CH, 4H) IR (hexane, cm$^{-1}$): $\nu$=2003.8 (m, CO); 1918.4 (w, CO); 1896.3 (s, CO); 1870.1 (m, CO)

Elemental analysis: $C_{17}H_{28}CrN_2O_4$ C: 54.24; H: 7.50, N: 7.44 (calculated); C: 54.85; H: 7.39; N: 6.94 (found).

The corresponding molybdenum and tungsten compounds were synthesized in an analogous manner from $Mo(CO)_6$ and $W(CO)_6$.

Example 4

Preparation of dicarbonylchloro(bis(diisopropylamino)-carbene)rhodium(I) by Means of a Ligand Exchange Reaction Carbon monoxide was passed through a yellow solution of chloro($\eta^4$-1,5-cyclooctadiene)(bis(diisopropylamino)carbene)rhodium(I) (300 mg, 0.65 mmol) in a 1:1 mixture of THF and toluene (35 ml) for 30 minutes. After the reaction solution had become brownish in color, the solvent was removed under reduced pressure and the crude product was washed with n-pentane. Yield: 68%.

$^1$H NMR (400 MHz, $CDCl_3$, 20° C.): $\delta$=4.11 (4H, NCH), 1.36 (24H, $CH_3$) $^{13}C\{^1H\}$ NMR (100.1 MHz, $CDCl_3$, 20° C.): $\delta$=221.7 (NCN, d, $^1$J(C—Rh)=64 Hz), 186.9 (CO, d, $^1$J(C—Rh)=74 Hz), 56.1 (NCH), 23.5 ($CH_3$).

MS (CI) m/e=406 (M$^+$, correct isotope pattern).

IR (KBr, cm$^{-1}$): $\nu$=2056 (s, CO), 1985 (s, CO).

Elemental analysis: ($C_{15}H_{28}ClN_2O_2Rh$, 406.76): calculated: C, 44.29, H, 6.93, N, 6.88; found: C, 44.32, H, 6.89, N, 6.91.

Example 5

Hydrosilylation of Acetophenone 0.61 ml of a stock solution of starting material (consisting of 0.8 ml of acetophenone, 1.3 ml of diphenylsilane and 300 mg of ferrocene as internal standard dissolved in 4 ml of $d_8$-THF together with 1 mol % of chloro($\eta^4$-1,5-cyclooctadiene)(bis(diisopropylamino)carbene)rhodium(I) as catalyst (as stock solution, 0.2 ml of $d_8$-THF) were placed in an NMR tube. After shaking vigorously, recording of the NMR kinetics was commenced immediately, with a $^1$H NMR spectrum being recorded every 10 minutes. The conversion was determined by integration of the relevant proton signals. The results are shown in Table 1.

TABLE 1

Hydrosilylation of acetophenone using various catalysts

| | Conversion of acetophenone [%] | | | |
|---|---|---|---|---|
| Time [min] | KD2 | KD1 | iPr-BIM | Cy-IM |
| 0.0 | 0.0000 | 0.0000 | 0.0000 | 0.0000 |
| 1.5 | 2.1083 | 5.3043 | 16.5262 | 49.7128 |
| 11.5 | 10.2384 | 19.7991 | 22.2451 | 63.8878 |
| 21.5 | 18.3888 | 27.1516 | 36.1491 | 64.2819 |
| 31.5 | 22.2013 | 40.4057 | 51.9386 | 64.4957 |
| 41.5 | 26.4179 | 50.1740 | 62.4524 | 64.6827 |
| 51.5 | 33.0257 | 57.5527 | 68.3399 | 65.2572 |
| 61.5 | 38.2527 | 63.9139 | 72.6104 | 65.6246 |
| 71.5 | 43.7828 | 68.4960 | 75.0390 | 66.2191 |
| 81.5 | 48.1140 | 72.3495 | 77.5176 | 66.6333 |
| 91.5 | 53.3275 | 75.7369 | 79.2908 | 66.8270 |
| 101.5 | 57.5778 | 78.5466 | 80.7767 | 67.2545 |
| 111.5 | 61.1949 | 80.5160 | 82.0191 | 67.2612 |
| 121.5 | 63.8488 | 81.5992 | 82.8307 | 67.4349 |
| 131.5 | 66.3142 | 82.0259 | 83.6486 | 67.5618 |
| 141.5 | 66.6038 | 82.4526 | 84.1668 | 67.7355 |
| 151.5 | 68.8199 | 82.6626 | 84.6663 | 67.9225 |
| 161.5 | 70.5914 | 82.7677 | 85.0846 | 67.8156 |
| 171.5 | 72.6122 | 82.9121 | 85.3843 | 68.0227 |
| 181.5 | 72.1137 | 83.1287 | 85.7402 | 68.1496 |
| 191.5 | 74.4308 | 83.2994 | 85.8900 | 68.1764 |
| 201.5 | 76.6941 | 83.5554 | 86.0586 | 68.3901 |

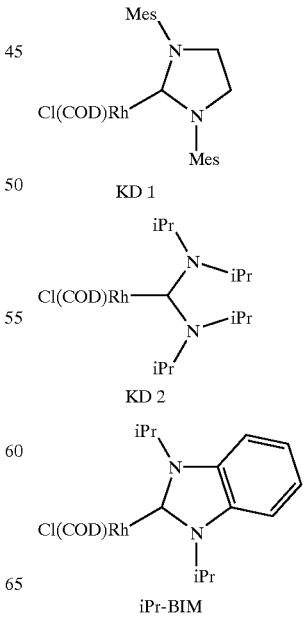

KD 1

KD 2 iPr-BIM

TABLE 1-continued

Hydrosilylation of acetophenone using various catalysts

| | Conversion of acetophenone [%] | | | |
|---|---|---|---|---|
| Time [min] | KD2 | KD1 | iPr-BIM | Cy-IM |

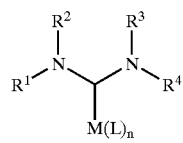

Cy-IM where COD is 1,5-cyclooctadiene, iPr is an isopropyl radical, Cy is a cyclohexyl radical and Mes is a mesityl radical.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Compound of the general structural formula (I), $$\begin{array}{c} R^2 \quad R^3 \\ | \quad \quad | \\ R^1{-}N{-}C{-}N{-}R^4 \\ | \\ M(L)_n \end{array} \quad (I)$$

where
  M is transition metal of transition groups 6 to 8 of the Periodic Table,
  $R^1$, $R^2$, $R^3$ and $R^4$ are identical or different and are hydrogen and/or hydrocarbon groups, where the hydrocarbon groups are identical or different, straight-chain, branched or cyclic radicals selected from the group consisting of alkyl radicals having from 1 to 50 carbon atoms, alkenyl radicals having from 2 to 50 carbon atoms, alkynyl radicals having from 2 to 50 carbon atoms and aryl radicals having from 6 to 30 carbon atoms in which at least one hydrogen atom is replaceable by a functional group, and/or
  $R^1$ and $R^2$ and/or $R^3$ and $R^4$ are part of a cyclic system which is identical or different, where the cyclic system comprises a carbon framework having from 2 to 20 carbon atoms and a nitrogen atom in formula (I), where the carbon atoms of $R^1$ and $R^2$ and/or $R^3$ and $R^4$ in formula (I) are not counted and where at least one hydrogen atom in the ring is replaceable by a functional group and/or at least one carbon atom of the ring is replaceable by a heteroatom selected from the group consisting of S, P, O and N, and/or
  $R^1$ and/or $R^2$ and/or $R^3$ and/or $R^4$ are linked to one of the ligands L via a bridge having from 1 to 20 carbon atoms, where the carbon atoms of $R^1$, $R^2$ $R^3$ and $R^4$ are not counted, and
  L is an identical or independently different uncharged two-electron donors and/or is a part of a cyclic system and/or is anionic ligands, and
  n is an integer.

2. Compounds according to claim 1, wherein L is an identical or independently different uncharged two-electron donor selected from the group consisting of amines, imines, phosphines, phosphites, stibines, arsines, CO, carbonyl compounds, nitriles, alcohols, thiols, ethers, thioethers and pyridines, and/or
  identical or independently different uncharged two-electron donor selected from the group consisting of N-heterocyclic carbenes of the general formula (A–E)

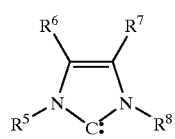

A

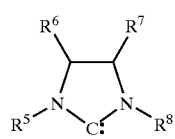

B

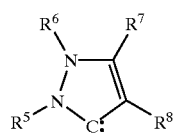

C

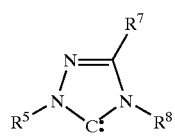

D

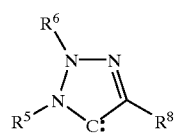

E where
  the radicals $R^5$, $R^6$, $R^7$ and $R^8$ are identical or different and are hydrogen and/or hydrocarbon groups, where the hydrocarbon groups are identical or different, straight-chain, branched or cyclic radicals selected from the group consisting of alkyl radicals having from 1 to 50 carbon atoms, alkenyl radicals having from 2 to 50 carbon atoms, alkynyl radicals having from 2 to 50 carbon atoms and aryl radicals having from 6 to 30 carbon atoms in which at least one hydrogen atom is replaceable by a functional group, and/or
  the radicals $R^6$ and $R^7$ are identical or independently different halogen, nitro, nitroso, alkoxy, aryloxy, amido, carboxyl, carbonyl, thio or/and sulfonyl groups, and/or
  identical or independently different uncharged two-electron donors selected from the group consisting of diaminocarbene ligands of the general formula (II),

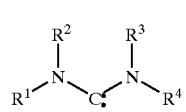

(II)

where
  the radicals $R^1$, $R^2$, $R^3$ and $R^4$ are as defined in claim 1, and/or identical or independently different uncharged two-electron donor ligands selected from the group consisting of compounds of the general formulae (III) and (IV)

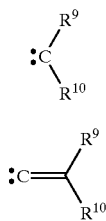

(III)

(IV)

where
the radicals $R^9$ and $R^{10}$ are identical or different and are hydrogen or/and hydrocarbon groups, where the hydrocarbon groups are identical or different, straight-chain, branched or cyclic radicals selected from the group consisting of alkyl radicals having from 1 to 50 carbon atoms, alkenyl radicals having from 2 to 50 carbon atoms, alkynyl radicals having from 2 to 50 carbon atoms, aryl radicals having from 6 to 30 carbon atoms and silyl radicals in which at least one hydrogen atom is replaceable by an alkyl, aryl, alkenyl, alkynyl, metallocenyl, halogen, nitro, nitroso, hydroxy, alkoxy, aryloxy, amino, amido, carboxyl, carbonyl, thio or/and sulfonyl group.

3. The compound according to claim 1, wherein L is an identical or independently different anionic ligand selected from the group consisting of halides, pseudohalides, hydroxides, alkoxides, thiolates, carboxylates and sulfonates.

4. The compound according to claim 3 wherein the pseudohalides are selected from the group consisting of cyanide, thiocyanate, cyanate, isocyanate and isothiocyanate.

5. The compounds according to claim 1, wherein L is a cyclic diene.

6. The compound according to claim 1, wherein M is rhodium or iridium and n is 3 and $L^1$, $L^2$ and $L^3$ are identical or/and independently different and/or are part of a cyclic system, where
$L^1$ is an anionic ligand selected from the group consisting of halide, alkoxide, carboxyl compound, thiolate and pseudohalide or is an uncharged two-electron donor selected from the group consisting of alkenes, alkynes, phosphines, amines, imines, phosphites, stibines, arsines, CO, carbonyl compounds, nitriles, alcohols, ethers, thiols and thioethers and
$L^2$ and $L^3$ are identical or independently different and are uncharged two-electron donors selected from the group consisting of alkenes, alkynes, phosphines, amines, imines, phosphites, stibines, arsines, CO, carbonyl compounds, nitriles, alcohols, ethers, thiols and thioethers or, are part of a cyclic diene.

7. The compound of claim 6 wherein $L^2$ and $L^3$ are part of a cyclic diene.

8. The compound of claim 6 wherein $L^2$ and $L^3$ together represent 1,5-cyclooctadiene.

9. The compound according to claim 1, wherein M is ruthenium or osmium and n is 4 and
$L^1$ and $L^2$ are identical or independently different and are each an anionic ligand selected from the group consisting of halide, alkoxide, carboxyl compound, thiolate and pseudohalide, with preferred pseudohalides being cyanide, thiocyanate, cyanate, isocyanate and isothiocyanate, and
$L^3$ is a carbene ligand of the general formula (III) or (IV) according to claim 2 and
$L^4$ is an uncharged two-electron donor selected from the group consisting of amines, imines, phosphines, phosphites, stibines, arsines, CO, carbonyl compounds, nitriles, alcohols, thiols, ethers and thioethers or is an uncharged two-electron donor ligand selected from the group consisting of N-hetrero-cyclic carbenes of the general formulae A–E according to claim 2 or is a diaminocarbene ligand of the general formula (II) according to claim 2.

10. Process for preparing the compound according to claim 1 comprising
a) preparing a carbene ligand of the formula (II) according to claim 2 by deprotonation of a formamidinium salt with strong bases or by the "ammonium method" and
b) reacting the carbene ligand of the formula (II) with suitable transition metal complexes in a ligand exchange reaction.

11. Process for preparing the compound according to claim 1 comprising reacting compounds of the type $[R^1R^2N—CH=NR^3R^4]^+X^-$, where $R^1$ to $R^4$ are as defined in claim 1, with transition metal complexes in a salt metathesis.

12. Process for preparing the compound according to claim 1 comprising reacting compounds of the type $[R^1R^2N—CH=NR^3R^4]^+X^-$, where $R^1$ to $R^4$ are as defined in claim 1, with alkali metal alkoxides and subsequently reacting the alkoxide adduct formed with transition metal complexes in a ligand exchange reaction.

13. A process for catalyzing hydrosilylation with the compound according to claim 1.

* * * * *